(12) United States Patent
Jung

(10) Patent No.: US 11,672,974 B2
(45) Date of Patent: Jun. 13, 2023

(54) CONTACTING METHOD AND SYSTEM

(71) Applicant: Heraeus Deutschland GmbH & Co. KG, Hanau (DE)

(72) Inventor: Markus Jung, Hanau (DE)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 109 days.

(21) Appl. No.: 16/708,750

(22) Filed: Dec. 10, 2019

(65) Prior Publication Data

US 2020/0179685 A1 Jun. 11, 2020

(30) Foreign Application Priority Data

Dec. 10, 2018 (DE) ...................... 10 2018 221 355.0

(51) Int. Cl.
*A61N 1/05* (2006.01)
*H01B 7/02* (2006.01)

(52) U.S. Cl.
CPC ............. *A61N 1/0587* (2013.01); *H01B 7/02* (2013.01); *A61N 1/0534* (2013.01)

(58) Field of Classification Search
CPC ................................ A61N 1/0587; H01B 7/02
See application file for complete search history.

(56) References Cited

U.S. PATENT DOCUMENTS

| 4,590,950 | A | 5/1986 | Iwaszkiewicz et al. |
| 7,364,479 | B1 | 4/2008 | Deily |
| 2002/0123748 | A1* | 9/2002 | Edwards ............ A61B 18/1477 606/41 |
| 2003/0195602 | A1* | 10/2003 | Boling ................. A61N 1/0539 607/122 |
| 2007/0168004 | A1* | 7/2007 | Walter ................. A61N 1/0551 607/116 |
| 2011/0218603 | A1 | 9/2011 | Victorine et al. |
| 2013/0338745 | A1 | 12/2013 | Ollivier et al. |
| 2014/0052229 | A1 | 2/2014 | Meadows et al. |
| 2014/0296951 | A1 | 10/2014 | Vetter et al. |

(Continued)

FOREIGN PATENT DOCUMENTS

| EP | 3185248 | 6/2017 |
| EP | 3185363 | 6/2017 |
| WO | 2015/031265 | 3/2015 |

*Primary Examiner* — Michael W Kahelin
(74) *Attorney, Agent, or Firm* — Dicke, Billig & Czaja, PLLC

(57) ABSTRACT

One embodiment relates to a system for reception and/or emission of an electrical signal from or into the human or animal body, including at least one insulated electrical conductor; a sleeve-shaped electrode that is electrically connected to the electrical conductor and includes an internal side, an external side, a channel, and an opening in a wall of the channel. The channel defines a longitudinal axis along which the conductor is arranged in the channel. A material of the electrode surrounds the entire circumference of the opening; the electrical conductor is guided through the opening between the internal side and the external side of the opening transverse to the longitudinal axis of the channel; and the electrical conductor is connected to the electrode within the opening directly in firmly-bonded and/or force-locking manner such that a durable mechanical and electrical connection between the electrical conductor and the electrode is established.

12 Claims, 3 Drawing Sheets

(56) References Cited

U.S. PATENT DOCUMENTS

| | | | |
|---|---|---|---|
| 2015/0088155 A1* | 3/2015 | Stahmann | A61N 1/3756 606/129 |
| 2016/0208114 A1 | 7/2016 | Hendricks et al. | |
| 2016/0303366 A1 | 10/2016 | Childers et al. | |
| 2017/0182310 A1 | 6/2017 | Troetzschel et al. | |
| 2017/0182311 A1 | 6/2017 | Keitel et al. | |

* cited by examiner

CONTACTING METHOD AND SYSTEM

CROSS-REFERENCE TO RELATED APPLICATION

This Utility Patent Application claims priority to German Application No. 10 2018 221 355.0 filed on Dec. 10, 2018, which is incorporated herein by reference.

TECHNICAL FIELD

One embodiment relates to a system for reception and/or emission of an electrical signal from or into the human or animal body, comprising at least one insulated electrical conductor; a sleeve-shaped electrode that is electrically connected to the electrical conductor and includes an internal side, an external side, a channel, and an opening in a wall of the channel, whereby the channel defines a longitudinal axis along which the conductor is arranged in the channel. Moreover, one embodiment relates to a method for contacting an electrical conductor.

BACKGROUND

The electrical contacting of an electrical conductor can often be a major challenge, in particular if dimensions are small. In this context, e.g., good electrical conductivity and mechanical stability even upon exposure to strong loads over an extended period of time are desired. This applies in particular to the electrical contacting of lines in medical devices. Referring to devices that are introduced into the human or animal body, it is desirable to use thin lines although these may be a challenge in terms of the electrical contacting due to their size. Another very important feature is the reliability of medical devices such as, e.g., cardiac pacemakers, implantable cardioverters, defibrillation devices, and cardiac resynchronisation devices, particularly with a view to keeping the material fatigue as low as possible. In particular the line and the electrical connectors are exposed to strong loads in operation.

Since invasive surgery is commonly required in order to introduce medical devices into the body or to remove or replace parts thereof, the individual components of the device are therefore desired to have a long service life in order to reduce the need for surgical interventions. EP3185248A1 describes a method for electrically contacting of a coated line to a particle. For this purpose, the insulation is partially removed and electrically conductive particles are introduced into a window (Via) generated in the process. The particle forms a conductive connection between the conductor and a ring electrode surrounding the conductor. In the process, creepage of the plastic insulation may lead to a loss of contact between the line and the particle though.

U.S. Pat. No. 7,364,479B1 describes a contacting method that is comparatively resource-consuming.

US2016303366 A1 describes the contacting that uses an additional connecting piece and therefore is resource-consuming as well.

US20130338745A1 describes a contacting by means of micro-slide. This is resource-consuming and can lead to an instability of the contact in practical application due to the manufacturing tolerances.

US20130338745A1 describes a contacting by means of ring electrodes, which include multiple hollow spaces for the electrical conductor. This method is resource-consuming and not very flexible.

In conventional methods it is often not possible to connect, especially, small structures of conductors and electrodes by means of a firmly-bonded connection, e.g. a welded connection, without damaging the plastic insulation of the conductor more than necessary. The connection of a conventional welded connection at the end of the electrode is susceptible to fatigue fracturing. Conventional crimp methods often destroy the surface structure of the electrode.

SUMMARY

It is the object of at least one embodiment to overcome the illustrated and further disadvantages of the prior art. For example, one embodiment provides an improved and simplified method for the electrical contacting of an electrode to a conductor that is advantageous especially in the micrometer range. The method is simpler and more flexible than methods of the prior art and delivers products with improved properties, as shall be illustrated in the following. Moreover, a system with an improved contacting between an electrical conductor and an electrode is provided. The improved contacting may be expressed, for example, in higher reliability, stability, and conductivity. In particular, one embodiment delivers a contacting with improved breaking strength and fatigue stability.

The objects are solved by the methods and systems described herein, in particular those that are described in the patent claims.

One embodiment is a system for reception and/or emission of an electrical signal from or into the human or animal body, including at least one insulated electrical conductor, a sleeve-shaped electrode that is electrically connected to the electrical conductor and includes an internal side, an external side, a channel, and an opening in a wall of the channel. The channel defines a longitudinal axis along which the conductor is arranged in the channel. A material of the electrode surrounds the entire circumference of the opening. The electrical conductor is guided through the opening between the internal side and the external side of the opening transverse to the longitudinal axis of the channel. The electrical conductor is connected to the electrode within the opening directly in firmly-bonded and/or force-locking manner such that a durable mechanical and electrical connection between the electrical conductor and the electrode is established.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 4A illustrates the partial ablation of the insulating layer of the conductor in order to expose one or more wires and enable a contacting.

FIG. 4B illustrates the severing of a conductor in order to form a free end.

FIG. 4C illustrates how multiple wires on the free end of the conductor are insulated from the conductor and are grasped out.

DETAILED DESCRIPTION

Figure 1:
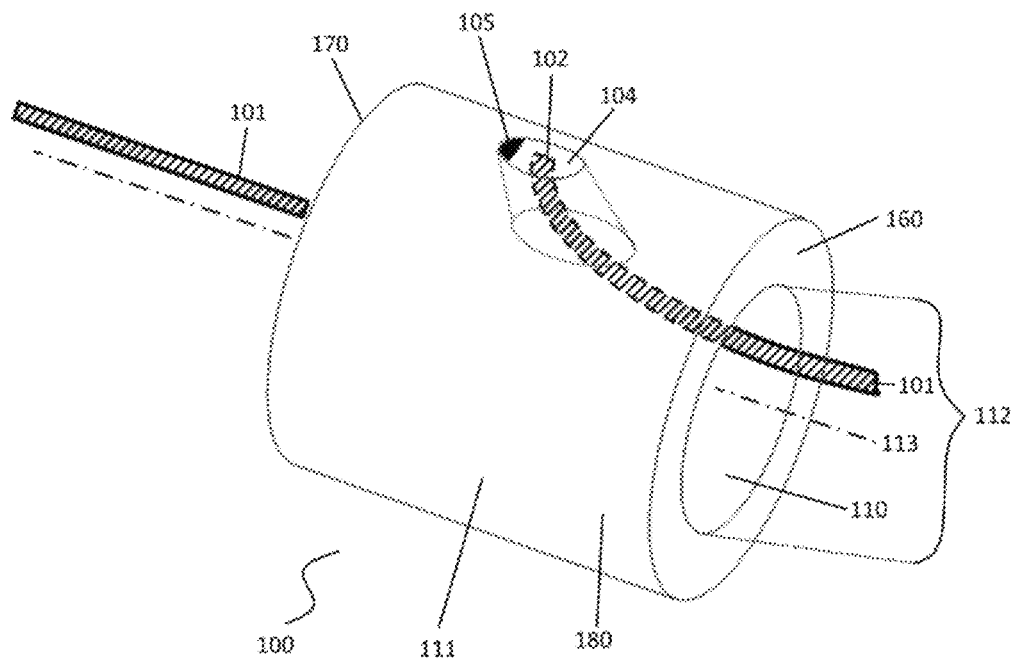
FIG. 1 illustrates a system according to one embodiment, in which an electrode and a conductor are electrically connected to each other.

In the following Detailed Description, reference is made to the accompanying drawings, which form a part hereof, and in which is illustrated by way of illustration specific embodiments in which one embodiments may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiments. The following detailed description, therefore, is not to be taken in a limiting sense, and the scope of the present embodiments are defined by the appended claims.

It is to be understood that the features of the various exemplary embodiments described herein may be combined with each other, unless specifically noted otherwise.

Referring to the embodiments described herein, whose elements "comprise" a certain feature (e.g. a material), a further embodiment shall also be considered as a matter of principle, in which the corresponding element consists of the feature alone, i.e. does not include any further components.

In as far as an element is referred to in the singular form in an embodiment, an embodiment, in which multiple of the elements are present, shall be considered as well.

Unless specified otherwise or clearly excluded by the context, it shall be possible as a matter of principle and shall herewith be taking into consideration unambiguously that features of different embodiments can also be present in other embodiments described herein. Moreover, it is considered, as a matter of principle, that all features described herein with reference to a method shall also be applicable to the products and devices described herein. Only for reasons of brevity, all of these considered combinations are not specified explicitly in all cases. Moreover, technical solutions known to be equivalent to the features described herein shall be included by the scope of embodiments as a matter of principle.

A first aspect of one embodiment relates to a system for reception and/or emission of an electrical signal from or into the human or animal body, comprising at least one insulated electrical conductor; a sleeve-shaped electrode that is electrically connected to the electrical conductor and includes an internal side, an external side, a channel, and an opening in a wall of the channel; whereby the channel defines a longitudinal axis along which the conductor is arranged in the channel; characterised in that a material of the electrode surrounds the entire circumference of the opening; the electrical conductor is guided through the opening between the internal side and the external side of the opening transverse to the longitudinal axis of the channel; and the electrical conductor is directly connected to the electrode within the opening in firmly-bonded and/or force-locking manner such that a durable mechanical and electrical connection between the electrical conductor and the electrode is established.

In one embodiment, the system is set up for reception of an electrical signal from the human or animal body. In one embodiment, the system is set up for emission of an electrical signal to the human or animal body. In one embodiment, the system is set up for both reception of an electrical signal from the human or animal body and for emission of an electrical signal to the human or animal body.

Moreover, the system can include a limit stop in the area of the opening.

Electrical Conductor

The electrical conductor can, for example, be an insulated metal wire. Accordingly, the conductor can include a metal wire and an insulation or consist of one or more metal wires and an insulation. In some embodiments, the conductor includes one or more of the metals Pt, Ir, Ta, Pd, Ti, Fe, Au, Mo, Nb, W, Ni, Ti, or a mixture and/or alloy thereof. In some embodiments, the conductor includes the alloys MP35, PtIr10, PtIr20, 316L, 301 or nitinol. The conductor can just as well include multilayered material systems. In some embodiments, the electrically conductive part of the conductor consists of one or more of the materials and an insulation. Suitable insulations are described in more detail in the following. In one embodiment, the conductor includes MP35, Au, Ta, Pt, Ir or Pd. In some embodiments, the electrically conductive part of the conductor consists of MP35, Au, Ta, Pt, Ir or Pd or alloys of the metals. In some embodiments, the conductor contains less than 3%, 2% or less than 1% Fe.

MP35 is a nickel-cobalt-based hardenable alloy. A variant of MP35 is described in the industrial standard ASTM F562-13. In one embodiment, MP35 is an alloy that includes 33 to 37% Co, 19 to 21% Cr, 9 to 11% Mo, and 33 to 37% Ni.

PtIr10 is an alloy made of 88 to 92% platinum and 8 to 12% iridium.

PtIr20 is an alloy made of 78 to 82% platinum and 18 to 22% iridium.

316L is an acid-resistant, CrNiMo austenitic steel with approx. 17% Cr; approx. 12% Ni and at least 2.0% Mo. One variant of 316L is described in the industrial standard EN 10088-2.

In one embodiment, 316L is an alloy that includes 16.5 to 18.5% Cr, 2 to 2.5% Mo, and 10 to 13% Ni.

301 is a chromium-nickel steel with high corrosion resistance. One variant of 301 is described in the industrial standard DIN 1.4310. In one embodiment, 301 is an alloy that includes 16 to 18% Cr and 6 to 8% Ni.

Nitinol is a nickel-titanium alloy with a shape memory with an ordered-cubic crystal structure and a nickel fraction of approximately 55%, whereby titanium accounts for the remaining fraction. Nitinol has good properties with regard to biocompatibility and corrosion resistance.

Unless specified otherwise, all percentages given herein shall be understood to be mass percentages (weight %).

The electrical conductor is electrically insulated. In as far as multiple electrical conductors are present, these include no electrical connection to each other. In some embodiments, the conductor includes a dielectric sheathing, for example made of an electrically insulating plastic material, silicone or rubber. Suitable plastic insulations include, for example, polyethylene, polyurethane, polyimide, polyamide, PEEK, and fluorinated plastics such as, e.g., ETFE, PTFE, PFA, PVDF or FEP.

Multiple conductors can be arranged into a conductor bundle.

Electrode

The electrode is a conductive, hollow and electrically conductive element, which can be attached appropriately as a sleeve to one or more conductors such that it surrounds the conductor or conductors or conductor bundle. The electrode can in one embodiment take the shape of a hollow cylinder or a similar shape. The electrodes are also referred to as "ring electrodes". In some embodiments, the electrode includes one or more of the metals Pt, Ir, Ta, Pd, Ti, Fe, Au, Mo, Nb, W, Ni, Ti, or a mixture and/or alloy thereof. In some embodiments, the electrode includes the alloys MP35, PtIr20, PtIr10, PdIr10, 316L, or 301. The electrode can just as well include multilayered material systems. In some embodiments, the electrode consists of one or more of the materials.

The electrode has an internal side that faces the part of the conductor that is guided in the channel, and an external side that faces away from the part of conductor that is guided in the channel.

In some embodiments, the electrode has an external diameter of less than 1.5 mm, in a specific embodiment it has an external diameter of less than 0.8 mm.

Opening

The electrode includes an opening. According to one embodiment, the material of the electrode surrounds the entire circumference of the opening. This means that the opening is appropriately arranged in the electrode such that the conductor guided therein cannot be moved laterally out of the opening (for example in the direction of the longitudinal axis of the channel) without first moving it along the longitudinal axis of the opening. This enables a stable and fatigue-free attachment of the conductor to the electrode. For example, the opening can be arranged essentially in central position in the wall of the channel, i.e. in the jacket surface of the electrode. By this means, the connection between the conductor and the electrode is more stable and fatigue-free. Accordingly, according to one embodiment, the opening does not touch the external edge of the electrode.

In one embodiment, the opening extends through-going from the internal side to the external side. As a result, a free end of the conductor can be guided fully through the jacket surface of the electrode. This enables a particularly stable attachment of the conductor to the electrode. Moreover, the implementation of the attachment is easier to attain.

Hereby, the electrical conductor can be guided through the opening from the internal side to the external side such that one end of the conductor is flush with the external side.

In one embodiment, the opening includes a varying diameter. For example, the opening can be cone-shaped. In one embodiment, the opening can include a smaller diameter on the external side than on the internal side. The opening tapering from the internal side to the external side of the electrode, in one embodiment tapering continuously, can be used, for example, for improved guidance of the conductor through the opening.

The opening is guided transverse to the longitudinal axis of the channel. The opening can extend either at a right angle or at a different angle with respect to the longitudinal axis of the channel. "Transverse" shall be understood to mean herein that two axes do not extend parallel with respect to each other, i.e. are arranged at an angle with respect to each other that differs from 0° or 180°, for example an angle from 1° to 179°. For example, the longitudinal axis of the opening can be arranged at an angle of 1° to 179° with respect to the longitudinal axis of the channel. In one embodiment, the angle is 2° to 188°, 5° to 185° or 10° to 170°. In one embodiment, the angle is 20° to 160°. In one embodiment, the angle is 40° to 140°. In one embodiment, the angle is 80° to 110°.

The opening can take different shapes at its surface. In one embodiment, the opening is essentially circular. In a further embodiment, the opening is essentially elliptical at the surface. In a further embodiment, the opening has the shape of a rounded triangle at the surface was tip is arranged in the direction of the free end of the conductor.

In one embodiment, the opening includes a diameter, at the surface, perpendicular to its longitudinal direction of less than 0.2 mm. In a further embodiment, the diameter of the opening is less than 0.1 mm. The diameter is at least 10 micrometres in size. In one embodiment, the diameter of the opening is larger than the diameter of the conductor. In one embodiment, the diameter of the opening is larger than the diameter of the why are in the conductor.

In one embodiment, the electrode includes multiple openings. The openings can extend essentially parallel, or at a different angle, with respect to each other relative to their respective longitudinal axes. The longitudinal axis of the opening extends from the internal side to the external side of the electrode.

In one embodiment, the opening includes a limit stop for holding an end of the conductor, in one embodiment the free end. For example, the conductor can be guided appropriately such that it hits against the limit stop. By this means, better fixation of the conductor can be attained. In one embodiment, the electrode includes a further opening, for example a total of 2, 3, 4, 5, 6, 10 or more than 10 openings.

Connection of the Electrode to the Conductor

A firmly-bonded connection can be attained, for example, by welding, brazing or soft soldering. In one embodiment, the firmly-bonded connection is a welded connection. The welded connection can be attained, for example, by laser welding. The melting of the conductor in the course of welding can be used to completely close the opening in the electrode. By this means, the ingress of liquids or other contaminations into the opening can be prevented. Moreover, sharp edges or burrs on the external side of the opening can be covered and therefore smoothed.

In one embodiment, the electrical conductor is connected to the electrode inside the opening in a force-locking manner. The force-locking connection can be achieved by clamping with pliers, crimping or swaging (drop forging) or other mechanical pressing methods known in this field. Several suitable methods are described in EP3185248A1. Comparable methods known in this context to a person skilled in the art can be used as well.

In one embodiment, the electrical conductor is connected to the electrode inside the opening in a direct firmly-bonded manner. In one embodiment, the electrical conductor is connected to the electrode inside the opening in a direct force-locking manner. In one embodiment, the electrical conductor is connected to the electrode inside the opening in a direct firmly-bonded as well as a direct force-locking manner. In one embodiment, the electrical conductor is connected to the electrode inside the opening in a direct firmly-bonded manner, but not in a force-locking manner.

Moreover, the electrical conductor can just as well be connected to the electrode within the opening in a form-fitting manner.

In one embodiment, the electrical conductor is connected to the electrode in a firmly-bonded manner, but not in a force-locking manner. The electrical conductor can just as well be connected to the electrode exclusively in a firmly-bonded manner. A firmly-bonded connection is preferred in one embodiment to be a welded connection. Having an exclusively firmly-bonded connection allows a deformation of the electrode to be prevented and simultaneously attains a very stable, durable and very conductive connection between the conductor and the electrode. This is of particular advantage in one embodiment if the electrode includes a certain surface structure and shall still maintain such structure after the contacting to the conductor. For example, particularly smooth electrode surfaces with a precisely defined geometry can be attained by this means.

In some embodiments, the electrode is micro-structured, i.e. it includes further surface structures in addition to the opening. The surface structures can impart a higher and precisely defined roughness to the electrode surface. The surface structures can be generated even before connecting the electrode to the conductor as they are not affected by a purely force-locking connection. This results in improved production procedures since the electrodes can be produced jointly from a metal tube, as shall be described in more detail herein. The metal tube can be structured and/or coated appropriately such that multiple structured and/or coated electrodes can be produced from the tube. It is also feasible to structure the electrode after attaching it to the conductor.

Similarly, it is feasible to use coated electrodes. According to the method according to one embodiment, in particular if the connection is of an exclusively firmly-bonded manner, a coating of this type is not affected by the inventive contacting of conductor to electrode. Moreover, the inventive connection (contacting) of the conductor to the centre of the electrode favours the fatigue behaviour of the connection effectively increasing the long-term stability of the connection.

In one embodiment, the system includes a multitude of electrical conductors that are each insulated with respect to each other and are arranged in the channel along the longitudinal axis, whereby the electrode surrounds multiple or all of the conductors.

In one embodiment, the system includes a multitude of electrodes, which each are electrically connected to exactly one other of the electrical conductors, such that the electrodes can be electrically addressed independent of each other. This means that each of the multitude of electrodes is set up to receive an electrical signal exclusively from exactly one conductor or to emit an electrical signal to the conductor, but not to any of the other conductors. Accordingly, each electrode can be electrically triggered independent of the other electrodes.

In one embodiment, the system includes both a multitude of electrical conductors that are each insulated from each other and are arranged in the channel along the longitudinal axis, whereby the electrode surrounds multiple or all of the conductors, and a multitude of electrodes, which each are electrically connected to exactly one other of the electrical conductors, such that the electrodes can be electrically addressed independent of each other.

In one embodiment, other than the direct connection between the conductor and the electrode, there is no further component present that connects the electrical conductor to the electrode in order to establish an electrical and mechanical connection in between. According to one embodiment, a welded or soldered connection or a material forming a connection of this type shall not be understood to be a "component" in this context. A component of this type could, e.g., be an additional loop or an additional crimp element such as, e.g., an additional sleeve, which is attached to the wire in order to subsequently connect it to the electrode.

In one embodiment, other than the direct connection between the conductor and the electrode and a limit stop, there is no further component present that connects the electrical conductor to the electrode in order to establish an electrical and mechanical connection in between.

There being no need for a component of this type renders the contacting of the conductor to the electrode simpler and less error-prone.

Medical Device

In a further aspect, one embodiment provides an electrical medical device, comprising a system according to any one of the preceding aspects and embodiments thereof.

The electrical medical device can, e.g., a lead, pulse generator, cardiac pacemaker, cardiac resynchronisation device, sensor or stimulator. Leads are electrical lines that can be used, for example, in medical application such as neuromodulation, heart stimulation, deep brain stimulation, spinal cord stimulation or gastric stimulation. In one embodiment, the lead is set up and/or intended to be connected to a generator of an active implantable device. A lead of one embodiment can just as well be used in a medical device for reception of an electrical signal. A stimulator is a medical device that can achieve a physiological effect by emitting an electrical signal to the body of a living being. For example, a neurostimulator can effect an electrical signal in a nerve cell (e.g. an action potential) by emitting an electrical signal to the nerve cell.

A further embodiment relates to a micro-electrode or a micro-electrode array that includes a system described herein.

Method

A further aspect of one embodiment relates to a method for electrically contacting an electrical conductor, comprising the following steps:

a. Providing a conductor and a sleeve-shaped electrode that includes an internal side, an external side, a channel, and an opening in a wall of the channel; whereby a material of the electrode surrounds the entire circumference of the opening;

b. unravelling the conductor such that the conductor includes a free end;

c. attaching the electrode to the conductor such that the conductor is arranged in the channel along the longitudinal axis thereof;

d. introducing the free end of the electrical conductor through the opening such that the conductor becomes arranged between the internal side and the external side of the opening transverse to the longitudinal axis of the channel;

e. connecting the electrical conductor to the electrode, whereby a durable mechanical and electrical connection between these is formed within the opening in a directly firmly-bonded and/or force-locked manner.

The method described above can include, in addition, a step a1, in which the insulation of the conductor is partially removed by ablation. In one embodiment, a rectangular area of the insulation of the conductor is removed. This can take place, for example, by laser ablation or similar methods. In this context, the width of the exposed surface can in one embodiment be equal to 0.5 to 2 times the conductor diameter and the length of the ablation can be equal to 2 to 8 times the wall thickness of the ring. In a further embodiment, the width of the ablation surface is equal to 1 to 1.5 times the diameter of the conductor (including the insulation) and the length of the ablation is equal to 2 to 4 times the wall thickness of the electrode. The ablation surface is preferred in one embodiment to be essentially rectangular in shape. In one embodiment, the width is defined transverse to the longitudinal axis of the conductor at the place of the exposed insulation and the length is defined parallel to the longitudinal axis of the conductor. In one embodiment, the length exceeds the width of the exposed surface.

The steps of the method can be implemented in the order given or in any different order. For example, step c can just as well be performed before step b.

In one embodiment, unravelling the electrical conductor, only the area of the wires of the conductor to be contacted is severed such that damage to the neighbouring wires is prevented. The neighbouring wires can, for example, be neighbouring wires within the same conductor or wires of a different neighbouring conductor in the spatial vicinity. In one embodiment, the insulation of the conductor is not severed completely during the unravelling such that the exposed surface is provided to be window-like and the remaining parts of the insulation cannot be shifted or twisted with respect to each other. Also in one embodiment, no wires other than the wires of the conductor to be contacted are severed in the area of the electrode to be contacted. This prevents the neighbouring conductors from being damaged.

If the conductor includes multiple single wires, the free ends of the wires are in one embodiment all connected appropriately to each other such that these free ends are limited to the smallest possible common space at the resulting connection site. The space is preferred in one embodiment to be smaller than the internal space of the opening and amounts to, e.g., half, a third, a fourth or a tenth of the volume of the opening. By this means, the conductor can be guided through the opening more easily.

In some embodiments, the internal side and/or the external side of the electrode are micro-structured or coated before and/or after being connected to the conductor.

The micro-structuring can effect a lower impedance or improve the electrical contact between conductor and electrode or the contact with the body of a living being. The surface can be structured, for example, by means of a laser. In one embodiment, the surface is enlarged by roughening the surface. This can take place with a variety of methods, for example by means of a laser.

A coating can effect a lower impedance or improve the electrical contact between conductor and electrode or the contact with the body of a living being. TiN, Ir, IrO$_x$, Pt or conductive polymers, for example conductive polymers based on thiophene, such as, for example, poly-3,4-ethylenedioxythiophene (PEDOT) or the conductive polymers described in WO/2015/031265, can be used for the coating. A coating can be effected, for example, by means of PVD, CVD or electrochemical deposition.

In some embodiments, the surface structure of the electrode is not impaired or impaired a little by the attachment. This is the case, for example, if no or a particular gentle clamping connection is used. This is advantageous in the embodiments specified above in that functions and/or effects generated by the coating and/or structuring are not being impaired.

In a further aspect, one embodiment provides a system for reception and/or emission of an electrical signal from and/or into the human or animal body that can be produced or is produced through a method according to the embodiments described herein. The system is characterised by an improved contacting of conductor and electrode and, if applicable, the further advantages described herein.

An electrode can be produced as follows, for example:

(1) Initially, drawing a metal tube from a suitable material, for example Pt, Ir, Ta, Pd, Ti, Fe, Au, Mo, Nb, W, Ni, Ti or alloys thereof, e.g. PtIr10, PtIr20, MP35, 316L, 301 or 304, as described herein, with the desired target diameter. (2) Then, ring electrodes of target length can be severed from the drawn tube, for example by means of laser cutting methods or mechanical cutting. (3) The opening can be generated, for example, by means of laser drilling, spark erosion or metal cutting methods. By this means, e.g. a ring electrode with a cone-shaped channel feedthrough through the ring wall can be produced.

The procedural steps described above of (2) cutting (severing) ring electrodes from the drawn metal tube and (3) drilling the opening can be implemented in any order, i.e. step (2) can be performed before or after step (3).

Alternatively, the electrode according to one embodiment can be produced through powder metallurgical procedures such as metal powder injection moulding, or additive procedures, such as selective laser melting, direct metal-laser sintering, laser deposit welding, electron-beam melting, lithography (also called bottom-up or build-up procedures).

The way and manner of the production of the electrode described above is a continuous procedure that does not require any specifically adapted tool. Accordingly, for example electrodes of different lengths can be produced without adapting a tool specifically to the length and/or without producing an adapted tool.

An electrical conductor can be produced from a plastic-insulated metal wire, as is known in this technical field. As a matter of principle, any known suitable method can be used for this purpose. If applicable, multiple insulated conductors of this type can be stranded to each other or bundled in other manner in order to arrange as many conductors as possible within the smallest possible total diameter. In one embodiment, the insulated conductors are arranged in a coil shape about a hollow space (also called coil structure).

A further aspect of one embodiment relates to a diagnostic method in or on the body of a living being, comprising the reception of an electrical signal by means of the system described herein.

A further aspect of one embodiment relates to the use of the system described herein in a diagnostic method in or on the body of a living being, comprising the reception of an electrical signal by means of the system.

A further aspect of one embodiment relates to a therapeutic method in or on the body of a living being, comprising the emission of an electrical signal by means of the system described herein.

A further aspect of one embodiment relates to the use of the system described herein in a therapeutic method in or on the body of a living being, comprising the emission of an electrical signal by means of the system.

The therapeutic method can include the emission of an electrical signal to nerve cells or muscle cells in the area of an organ, for example heart, muscle, stomach or brain.

The diagnostic method can include the reception of an electrical signal from nerve cells or muscle cells in the area of an organ, for example heart, muscle or brain.

Examples

One embodiment is illustrated further in the following based on examples, though these may not be construed such as to limit embodiments in any way or form. It will be obvious to a person skilled in the art that, in place of the features described herein, other equivalent means can be used in like manner.

FIG. 1 illustrates a system 100 according to one embodiment in exemplary manner. The system is set up to emit an electrical signal to the human or animal body or to receive an electrical signal from the human or animal body, or both. An insulated electrical conductor 101 is guided along a longitudinal axis 113 of a channel 112 within an electrode 103. The channel 112 forms the internal space of the electrode 103. The channel is surrounded by a wall 160. The electrode 103 includes an internal side 110 and an external side 111 and is, for example, designed to be essentially cylindrical, i.e. sleeve-shaped (also called ring electrode). The conductor 101 includes a free end 102, which is guided through an opening 104 in the wall 160. The electrode includes a ring-shaped edge 160 each in the area of the channel openings. The opening 104 is appropriately arranged in the electrode 103 such that a material of the electrode 103 surrounds the entire circumference of the opening 104, i.e. the edge of the opening 104 extends completely on a jacket surface 190 on the external side 111 of the electrode 103. The opening 104 therefore does not touch the edge 170 of the electrode 103. By this means, the conductor cannot possibly be torn in lateral direction out of the opening, if the connection between conductor and electrode breaks. The longitudinal axis 113 of the channel 112 extends transverse to the longitudinal axis of the opening 104 such that the conductor 101 in the area of the opening 104, i.e. between the internal side 110 and the external side 111, is guided transverse to the longitudinal axis 113 through the opening 104. The opening 104 can essentially be cylindrical or in one embodiment be cone-shaped. The opening 104 tapering in a cone shape from the internal side 110 to the external side 111 can simplify the guidance of the conductor 101 through the opening 104 or enable an improved attachment. The opening 104 is in one embodiment dimensioned appropriately such that the conductor 101 can be guided through the opening 104 by its free end 102, and subsequently can be connected to the electrode through a force-locking and/or form-fitting connection. Examples of suitable dimensions of the opening 104 are described herein. The conductor 101 is being connected to the electrode 103 within the opening 104 in directly firmly-bonded and/or force-locking manner. The connection keeps the conductor 101 durably safe in the opening 104 and provides for a stable and error-free electric connection between conductor 101 and electrode 103. In one embodiment, the connection is designed appropriately such that the opening 104 is hermetically closed, i.e. is liquid-tight, for example. This can be attained, for example, through a welded connection, but a connection by brazing or soft soldering is feasible just as well. The connection can also be established by clamping, for example crimping, clamping with pliers or swaging (also called drop forging) of the conductor 101 in the opening 104. The connection can also be attained through a combination of welding and clamping. In one embodiment, the connection contains no further elements other than the conductor 101, the electrode 103, and a welded connection. In one embodiment, the conductor 101 is connected to the electrode 103 exclusively through a welded connection.

The opening 104 can include a limit stop 105 in the area of its external side 111. The limit stop can simplify the positioning of the free end 102 of the conductor 101, when the free end 102 is being guided through the opening 104. Moreover, the limit stop can additionally secure the connection of the conductor 101 in the opening 104. By this means, the stability of the connection between the conductor 101 and the electrode 103 can be improved.

Figure 2:
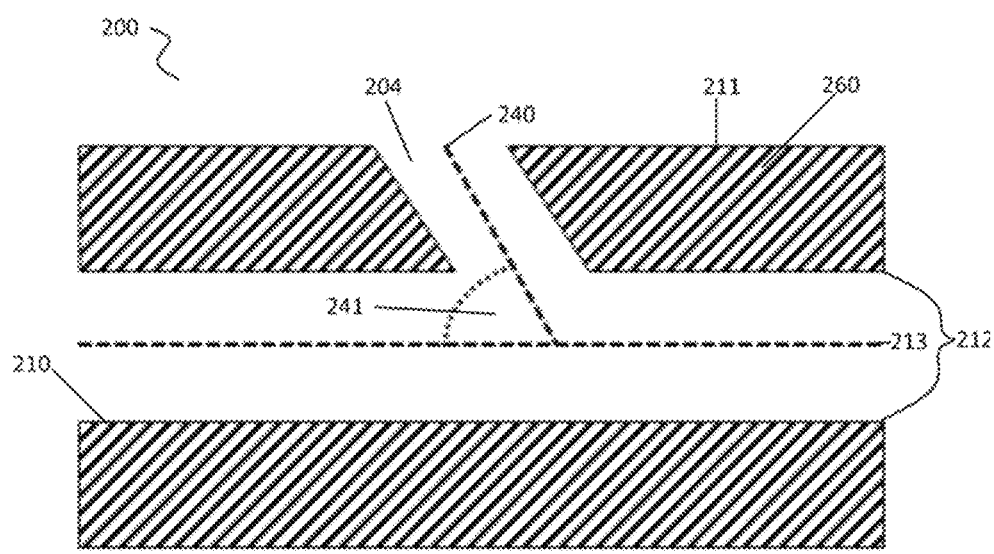
FIG. 2 illustrates a cross-section through a system according to one embodiment.

FIG. 2 illustrates a cross-section through a system 200 according to one embodiment. The conductor is not illustrated. A channel 212 extends along a longitudinal axis 213. An opening 204 extends from the internal side 210 to the external side 211 of the electrode along a longitudinal axis 240. The longitudinal axis 213 of the channel 212 forms an angle 241 with respect to the longitudinal axis of the opening 204 such that the longitudinal axis 213 is arranged transverse with respect to the longitudinal axis 204.

Figure 3:
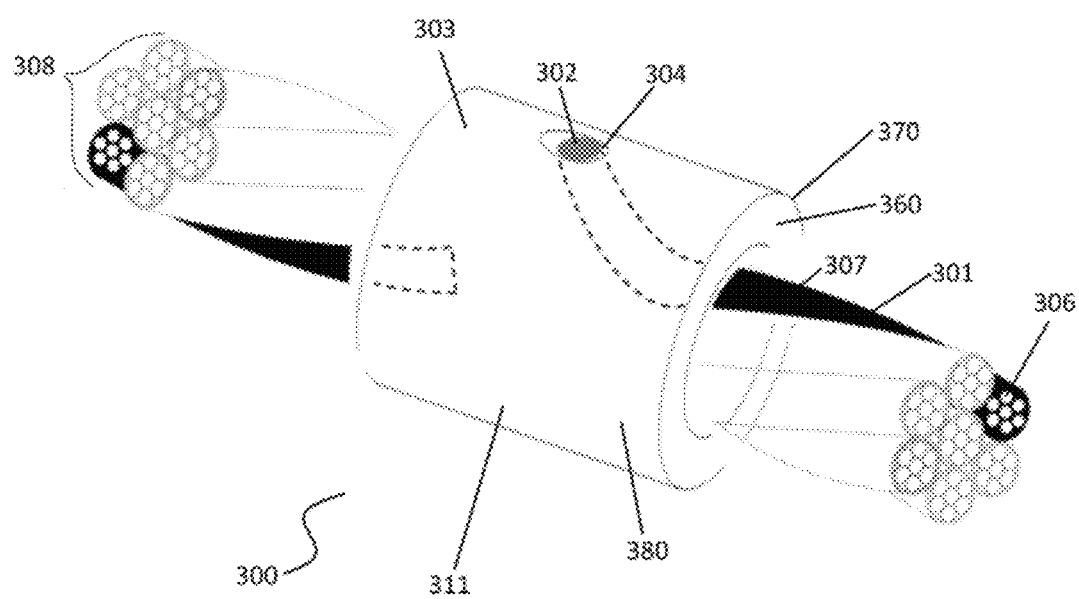
FIG. 3 illustrates a particular development of the system according to one embodiment, in which multiple conductors are stranded to each other and each of the conductors includes multiple wires.

FIG. 3 illustrates an embodiment, in which a system 300 according to one embodiment includes multiple insulated conductors 301, whereby each conductor 301 includes one or more wires 306. The conductors 301 form a conductor bundle 308. The electrode 303 surrounds the entire conductor bundle 308. The wires 106 can consist, for example, of a conductive metal such as, e.g., platinum or a platinum alloy. The wires 306 within the same conductor 301 can be conductively connected to each other. The insulated conductor 301 includes an insulation 307, for example a plastic layer, that surrounds all wires 306 of the conductor 301. The various conductors 301 are electrically insulated from each other by means of the insulation 307 which allows them to be electrically addressable individually and independent of each other. A conductor bundle 408 can include multiple conductors 301 that are, for example, stranded to each other or are essentially arranged coil-like (coil structure). In one embodiment designed as a ring electrode, the electrode 303 surrounds the entire conductor bundle 308 in each case. Multiple electrodes 303 can be arranged at different positions of the same conductor bundle 108. The electrodes 303 can be set up to receive an electrical signal, emit an electrical signal or both of these at various positions independent of each other. The electrodes 303 can be electrically addressable individually by various conductors 301 of the same system. As a result, the signal reception or emission on an electrode 303 does not affect other electrodes 303 of the system 300. Accordingly, multiple electrodes 303 can be used independent of each other for reception or emission of different electrical signals, whereby these signals do not affect each other even if they are transmitted simultaneously in the same system 300. A free end 302 of the conductor 301 can be guided appropriately through the opening 304 such that the free end 302 is flush with an external side of the electrode 311.

Figure 4A:
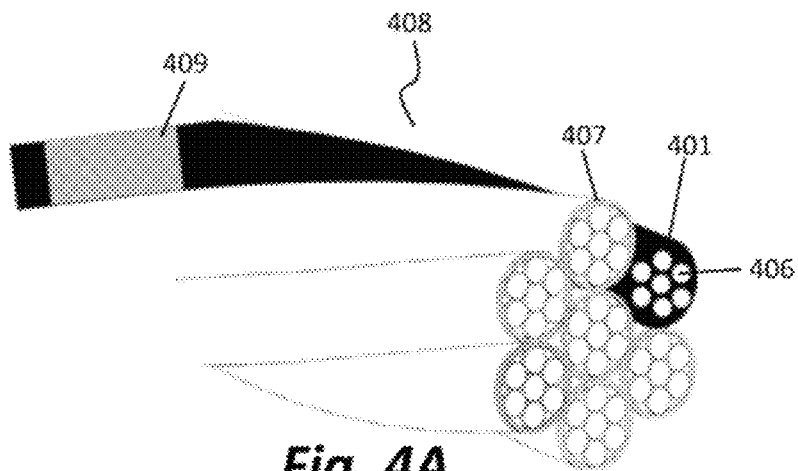
FIGS. 4A, 4B, 4C illustrate steps of a method according to one embodiment.
Figure 4B:
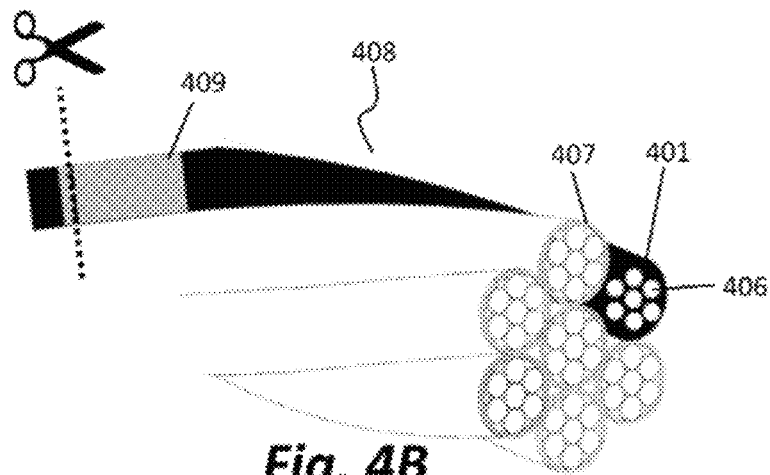
Figure 4C:
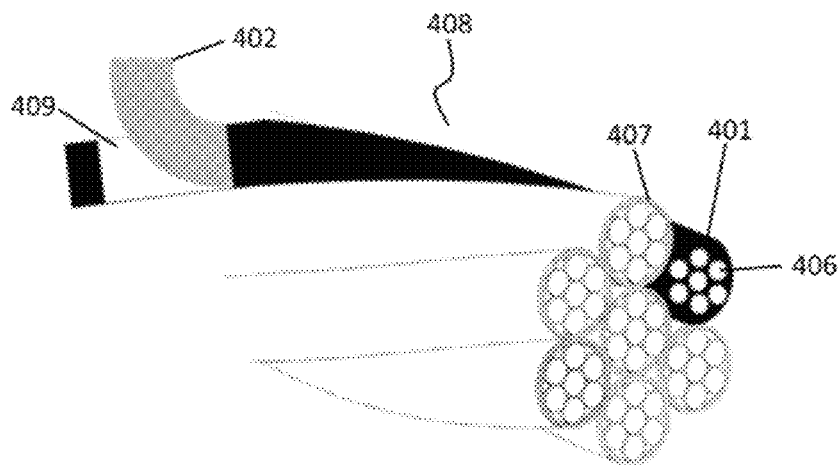

FIGS. 4A, 4B and 4C illustrate steps of the production of the system according to one embodiment. For this purpose, an insulated conductor 401 and a sleeve-shaped electrode (not illustrated in FIGS. 4A to 4C) are provided initially. In one embodiment, a conductor bundle 408 is formed from multiple conductors 401, as described above. The conductor 401 includes an insulation 407. The electrodes 103 and 303 from FIGS. 1 and 3 and the embodiments described above can be used. The electrode can be produced as described above. In this context, the electrode is drilled appropriately such that an opening is formed in the jacket surface of the electrode through which a free end 402 of a conductor 401 can be guided. Multiple openings can be drilled in the electrode just as well. If the drill drilling the opening is not guided fully through the electrode, the opening can include a residual part of the electrode material on the outside that forms a limit stop for the conductor 401, in particular for the free end 402 thereof. The electrode is attached appropriately to the conductor 401 or a conductor bundle 408 such that the electrode surrounds the conductor 401 or the entire conductor bundle 408 in ring-shaped manner, i.e. the electrode is plugged onto the conductor bundle 408. In other words, the conductor bundle 408 is guided through the channel of the electrode. The electrode is then shifted to the desired position of the conductor bundle 408 at which it is to be contacted to the conductor 401. Referring to multiple electrodes, these steps are repeated appropriately such that multiple electrodes are situated at different desired positions of the conductor bundle 408. For example, the electrodes, originating from an end of the conductor bundle 408, can be arranged other on the conductor bundle 408 at regular distances with respect to each.

The insulation of the conductor 401 is exposed in a section 409 by laser ablation such that the wires 106' below it are partially exposed (FIG. 4A). The section 409 is therefore a surface of the conductor 401 from which the insulation 407 has been removed. The section 409 can take the shape of a rectangle or cuboid. Subsequently, one of the wires 406 of the conductor 401 is severed, for example by means of laser cutting (FIG. 4B). Other methods can be used for severing the conductor 401 just as well. Laser cutting is advantageous in this context since it enables high precision. In one embodiment, only one of the wires 406 is being severed in this context. In one embodiment, the plastic insulation 407 of the conductor 401 is not severed while the conductor 401 is being severed such that only a window in the insulation 407, i.e. the section 409, is exposed (FIG. 4A). Accordingly, the insulation 407 in one embodiment remains untouched except for the window arising from ablation. As illustrated in FIG. 4C, the severed wire 406 of the conductor 401 is carefully guided out of the conductor 401 by its free end 402. The free end 402 is now guided through the opening from the internal side to the external side of the electrode and moved to a position, in which a stable electrical and mechanically durable connection between the free end 402 and the electrode can be formed. In one embodiment, the free end 402 should be guided fully or almost fully through the opening for this purpose. Subsequently, the free end 402 of the wire 406 is being connected to the electrode by welding in the area of the opening. In one embodiment, the free end 402 does not protrude or protrude only little from the opening on the external side. The free end can, for example, be flush with the external side. The connection can just as well be effected by means of a force-locking connection, for example by compressing the opening in order to hold the wire 406 in a force-locking manner. A combination of the two connection methods can be used just as well. In one embodiment, the wire 406 is being welded within the opening such that the molten material of the wire 406 and/or of the electrode partially or completely fills the intervening spaces between the wire 406 and the electrode in the area of the opening such that a stable electrical and mechanically durable connection between the free end 402 of the wire 406 and the electrode can be formed. In one embodiment, the material molten during the welding covers the entire external side of the opening. Also in one embodiment, the material molten during the welding covers the burr of the border line on the external side of the opening in order to prevent sharp edges on the external side of the system.

The electrode can be micro-structured just as well, for example by means of a laser, as described elsewhere herein. The procedural step can take place before or after contacting the electrode to the conductor. The micro-structuring can, for example, increase the surface roughness in order to facilitate a better connection to other materials. The electrode can just as well be coated with a further material, as described in detail elsewhere herein. The procedural step can take place before or after contacting the electrode to the conductor. In some embodiments, the electrode is first being micro-structured and then coated. A micro-structuring of the coating can take place just as well. In one embodiment, the contacting of the conductor to the electrode takes place exclusively through a welded connection, and subsequently the electrode is being micro-structured and/or coated. The coating can improve the reception or emission of an electrical signal or the biocompatibility.

Although specific embodiments have been illustrated and described herein, it will be appreciated by those of ordinary skill in the art that a variety of alternate and/or equivalent implementations may be substituted for the specific embodiments illustrated and described without departing from the scope of the present embodiments. This application is intended to cover any adaptations or variations of the specific embodiments discussed herein. Therefore, it is intended that these embodiments be limited only by the claims and the equivalents thereof.

REFERENCE TESTS

A system according to one embodiment was subjected to a tensile strength test in a Mecmesin Multitest 1, whereby the breaking strength was determined at a drawing rate of 4 mm/min. The breaking strength corresponds to the tensile force at which the connection between conductor and electrode tears off. Three samples were tested in this context:

Sample A (reference sample): The ring electrode was crimped onto the conductor.

Sample B (reference sample): The conductor was welded to an external edge of the ring electrode.

Sample C (according to one embodiment): A free end of the conductor was guided through an opening in the electrode, swaged, and welded within the opening.

The measured breaking strength values are listed in Table 1 below. Sample C (according to one embodiment) illustrated clearly improved breaking strength (breaking force) as compared to the reference samples.

TABLE 1

Test results of the breaking force tests

| | Sample | | |
|---|---|---|---|
| | A (Reference) | B (Reference) | C (Invention) |
| Breaking force | 3N | 2N | 8N |

The invention claimed is:

1. A system for reception or emission of an electrical signal from or into the human or animal body, comprising:
   at least one insulated electrical conductor;
   a sleeve-shaped ring electrode that is electrically connected to the electrical conductor and comprises an internal side, an external side, a channel; and
   an opening in a wall of the channel, wherein the opening has a smaller diameter at the external side than its diameter at the internal side;
   wherein the channel defines a longitudinal axis along which the conductor is arranged in the channel;
   wherein a material of the ring electrode surrounds the entire circumference of the opening;
   wherein the electrical conductor is guided through the opening between the internal side and the external side of the opening transverse to the longitudinal axis of the channel;

wherein the electrical conductor is connected and fixed to the ring electrode within the opening directly in firmly-bonded or force-locking manner such that a durable mechanical and electrical connection between the electrical conductor and the ring electrode is established and such that no portion of the electrical conductor extends beyond the external side of the ring electrode; and wherein, other than the direct connection between the conductor and the ring electrode, there is no further component present that supports the connection of the electrical conductor to the ring electrode in order to establish a mechanical connection in between.

2. The system according to claim 1, wherein the firmly-bonded connection is a welded connection.

3. The system according to claim 1, wherein the electrical conductor is connected to the ring electrode in a firmly-bonded, but not in a force-locking manner.

4. The system according to claim 1, comprising a multitude of electrical conductors that are each insulated with respect to each other and are arranged in the channel along the longitudinal axis, wherein the ring electrode surrounds multiple or all of the conductors.

5. The system according to claim 4, comprising a multitude of ring electrodes, which each are electrically connected to exactly one other of the electrical conductors, such that the ring electrodes can be electrically addressed independent of each other.

6. The system according to claim 1, wherein the opening extends through the ring electrode going from the internal side to the external side.

7. The system according to claim 6, wherein the electrical conductor is guided through the opening from the internal side to the external side such that one end of the conductor is flush with the external side.

8. The system according to claim 1, wherein the opening has a varying diameter that is cone-shaped.

9. The system according to claim 1, further comprising at least one further opening.

10. An electrical medical device comprising a system according to claim 1.

11. The electrical medical device according to claim 10 that is at least one of a lead, a pulse generator, a cardiac pacemaker, a cardiac resynchronisation device, a sensor and a stimulator.

12. A method of treatment of a human or animal body, comprising the emission of an electrical signal by the system according to claim 1.

* * * * *